United States Patent [19]

Allen

[11] 4,294,731

[45] Oct. 13, 1981

[54] METHOD FOR DRYING ABSORBENT MODIFIED CELLULOSIC POLYMERS AND THE LIKE

[75] Inventor: Thomas C. Allen, Asheville, N.C.

[73] Assignee: Akzona Incorporated, Asheville, N.C.

[21] Appl. No.: 177,678

[22] Filed: Aug. 13, 1980

Related U.S. Application Data

[63] Continuation of Ser. No. 39,725, May 17, 1979, abandoned.

[51] Int. Cl.³ ............................................... C08L 1/00
[52] U.S. Cl. ........................... 260/17.4 CL; 106/169; 106/186; 106/188; 106/189; 260/17.4 GC; 260/17.4 ST; 536/32; 536/43; 536/48; 536/50; 536/59; 536/61; 536/62; 536/66; 536/87; 536/97; 536/101; 536/108; 536/109; 536/110; 536/89; 536/91; 106/210; 106/213
[58] Field of Search ............... 106/169, 186, 188, 189, 106/210, 213; 260/17.4 GC, 17.4 CL, 17.4 ST; 536/32, 43, 48, 50, 59, 61, 62, 66, 87, 97, 101, 108, 109, 110

[56] References Cited

U.S. PATENT DOCUMENTS

| | | | |
|---|---|---|---|
| 3,256,372 | 6/1966 | Adams et al. | 264/28 |
| 3,376,285 | 4/1968 | Callihan et al. | 536/87 |
| 3,489,719 | 1/1970 | Savage et al. | 536/87 |
| 3,505,257 | 4/1970 | Conte et al. | 536/60 |
| 3,589,364 | 6/1971 | Dean et al. | 427/180 |
| 3,658,790 | 4/1972 | Bernardin | 536/34 |
| 3,691,154 | 9/1972 | Bernardin | 536/62 |
| 3,907,499 | 9/1975 | Ingram et al. | 8/181 |
| 3,997,647 | 12/1976 | Lassen | 260/17.4 CL |

*Primary Examiner*—Melvyn I. Marquis
*Attorney, Agent, or Firm*—Francis W. Young; Jack H. Hall; Alan R. Stempel

[57] ABSTRACT

A method for oven drying chemically modified cellulosic materials, especially fibers, having improved fluid absorbency involves incorporating into the cellulose structure while swollen an amphiphilic compound miscible with water which will not evaporate when the fiber is oven dried and will remain in the fiber to prevent collapse of the fiber as the water is removed. The improved method of drying the fibrous cellulosic material produces a product having saline absorbency about equal to that produced when the fibers are dried with a water-miscible solvent and avoids the use of volatile solvents and the disadvantages inherent therewith. The fibers provided by the invention are especially suitable for use in pads which are to be used for absorbing water and body fluids.

18 Claims, No Drawings

METHOD FOR DRYING ABSORBENT MODIFIED CELLULOSIC POLYMERS AND THE LIKE

This is a continuation of application Ser. No. 039,725, filed May 17, 1979 and now abandoned.

This invention relates generally to highly absorbent cellulosic and starch materials and, more particularly, to an improved method of drying of cellulose and starch materials modified by the introduction of chemical groups more hydrophilic than the hydroxyl groups thereof, without significant adverse effect on the fluid absorbency characteristics of the fibers.

It has been previously proposed to increase the hydrophilic properties of polymers containing hydroxyl groups such as cellulose and starch by substituting more hydrophilic groups such as carboxylic acid, phosphoric acid, sulfuric acid, sulfonic acid or carboxylic acid amide groups along the polymer backbone for hydroxyl groups. For example, bibulous wet cross-linked fibrous salts of carboxymethylcellulose having a sufficiently high degree of carboxymethyl substitution to insure water solubility in the absence of cross-linking are disclosed in U.S. Pat. No. 3,589,364. Phosphorylated cellulose pulp fibers are disclosed in U.S. Pat. Nos. 3,658,790 and 3,691,154. In accordance with the disclosure in U.S. Pat. No. 3,658,790, highly absorbent fibers are prepared by chemically substituting phosphate groups for hydroxyls on the cellulose, hydrolytically degrading the fiber walls and then converting the partially substituted and hydrolyzed cellulose fibers to the salt form by ion exchange. The phosphorylated cellulose fibers are dried by displacing the water with a water-miscible liquid such as an alcohol or a ketone. In U.S. Pat. No. 3,997,647, chemically modified cellulose fibers such as those disclosed above or below are made even more absorbent by refining in the presence of water, centrifuging to remove unbound water, and extruding into filaments. These filaments are also dried by displacing water with a water-miscible liquid.

It has also been proposed before to improve the absorbency of fibers of cellulose by chemically modifying the cellulose with graft polymer side chains on the cellulose back-bone. For example, it is proposed in U.S. Pat. No. 3,661,815 to use granular, water-insoluble alkali metal carboxylate salts produced by the saponification of starch-acrylonitrile graft co-polymers in the manufacture of disposable paper pads. The alkali metal carboxylate salts are described as substances which increase the water absorbency of the pads. In U.S. Pat. No. 3,505,257, a process for preparing graft co-polymers of ethylenically unsaturated compounds and cellulosic or amylaceous materials is disclosed. This patent further states that if the graft co-polymer is made from acrylic acid, the property of improved water absorbency is imparted to the material. Many other processes for the preparation of graft co-polymers, all with the capability of using hydrophilic ethylenically unsaturated monomers or precursors of such monomers, are disclosed in the literature, some examples of such being U.S. Pat. Nos. 2,922,768; 3,357,933; 3,330,787; 3,359,224; and 3,889,678. In U.S. Pat. No. 3,256,372, modified cellulosic products having very high capacity to absorb and retain water are prepared by the formation or deposition therein of polymers containing hydrophilic functional groups.

The substituted and grafted materials disclosed in the above references are prepared in water and must be dried before they can be used in aqueous fluid absorbent articles. However, it has been found in practice that if the water is removed by a normal heat drying process, the cellulosic material, having the open structure brought about by the substitution, tends to collapse as water evaporates. It is believed that hydrophilic groups introduced into the polymer and the hydroxyl groups thereof tend to hydrogen bond to retain the structure in its collapsed state, thus reducing the absorbency or the amount of water that can re-enter the structure on rewetting. However, if the open structure can be retained, that is, its collapse avoided during drying, hydrogen bonding is discouraged. The extensive hydrogen bonding also tends to make the new material quite stiff and brittle, reducing the effectiveness of the material for use in consumer products such as tampons, sanitary napkins, diapers, medical sponges, absorbent wipes, and the like.

In order to overcome these two problems, a number of non-conventional drying methods have been proposed. For example, it is stated in U.S. Pat. No. 3,658,790 that "for best results, it is preferred that the pulp fibers, which expand and swell during wet refining, retain an expanded state when dried. Ordinarily, when a swelling liquid is removed from swelled cellulose fibers by evaporative drying, the swollen structure collapses to its non-swollen state. Solvent drying minimizes such collapse. Freeze drying accomplishes this objective also, . . . In any event, the fibers should be dried by physical removal of the water by means other than evaporation. Ordinary evaporative drying from a wet state is not desirable since the resulting fibers form hydrogen bonds resulting in a horny, hard mass which does not exhibit the desired improvement in absorbency to any significant degree even when mechanically reduced to fibers." The highly absorbent webs produced in U.S. Pat. No. 3,997,647 are also solvent dried. The same drying problems are also present with cellulosic fibers modified by the polymerization therein of ethylenically unsaturated monomers containing hydrophilic groups. For example, it is stated in U.S. Pat. No. 3,256,372 that "It is important that the wet molded objects formed from the pastes or slurries described above are dried under suitable conditions whereby the pore structure is maintained. If these wet objects are permitted to dry in air or in an oven at atmospheric pressures, the pore structure will collapse and the resultant product will be dense and nonuniform." Further descriptions of the problems involved in the irreversible drying of cellulose and its hydrophilic modified derivatives are found throughout the literature. One particularly useful and comprehensive source is found in "A Review of the Literature on the Effect of Caustic Soda and Other Swelling Agents on the Fine Structure of Cellulose," by J. O. Warwicker, R. Jefferies, R. L. Colbran, and R. N. Robinson, Shirley Institute Pamphlet No. 93, The Shirley Institute, Didsbury, Manchester, December, 1966.

As explained above, in order to avoid the problems involved in the evaporative drying method of removing water from fibers for use in absorbent pads, it has been proposed to displace the water with a water-miscible, non-aqueous solvent such as a water miscible monohydric alcohol or ketone, e.g. 2-propanol or acetone. A common explanation for the mechanism involved is that the bulky solvent molecules replace the water in the polymer structure and prevent hydrogen bonding between the hydrophilic groups, retaining the open fiber structure and absorbency properties as well as the soft, pleasant feel of the material. However, such a non-conventional drying process has obvious disadvantages. Processing conditions are more complex and difficult to control and precautions must be taken to avoid ignition of the solvent and exposure of personnel to toxic fumes. Moreover, it is necessary to provide a solvent recovery system in order to minimize the increased costs involved in drying with a solvent instead of by a conventional oven drying process.

It is an object of this invention to provide an improved method for drying cellulosic or starch materials which have been modified by the addition of hydrophilic groups, either by chemical substitution of the hydroxyl group or by graft or in situ polymerization of appropriate monomers. Another object of the invention is to provide a method for drying water wet cellulosic materials, which have been modified to contain hydrophilic groups, by evaporation of the water therefrom to thereby avoid the disadvantages of the heretofore known hot air drying processes. Still another object of the invention is to provide a method for drying cellulose fibers containing hydrophilic groups by evaporation of the water without substantial collapse of the cellulose and without substantial irreversible hydrogen bonding. A more specific object of the invention is to provide a method for hot air drying phosphorylated cellulose fibers which produces a highly absorbent product to be used to advantage for the absorption of body fluids or water.

The cellulosic or starch materials modified by the chemical substitution of more hydrophilic groups for the hydroxyl group can be prepared by the procedures described in U.S. Pat. Nos. 3,997,647; 3,658,790; or 3,589,364. Examples of specific hydrophilic groups are phosphate, sulfate, carboxymethyl, carboxyethyl, carboxamide, and the like. The degree of substitution on the cellulose can vary within a wide range as described in the above references, but in general the higher the degree of substitution of hygrophilic groups, the greater the drying problem.

The cellulosic or starch materials modified by the graft or in situ polymerization of appropriate monomers can be prepared by the procedures described in U.S. Pat. Nos. 3,505,257; 3,359,224; 3,357,933; 3,661,815; 2,922,768; 3,256,372; and 3,889,678 and Brickman, W. James, "Continuous Thiocarbonate-Redox Grafting on Cellulosic Substrates," pp. 9–27, in *Cellulose Technology Research*, Albin F. Turbak, Ed., ACS Symposium Series 10, American Chemical Society, Washington, D.C. 1975. Suitable monomers for this modification are acrylic acid, methacrylic acid, acrylamide, methacrylamide, 2-acryloamido-2-methylpropane sulfonic acid, vinyl sulfonate, itaconic acid, maleic acid, itaconic acid, 2-hydroxyethyl methacrylate sulfate, 2-hydroxyethyl methacrylate phosphate, 2-hydroxyethyl acrylate sulfate, 2-hydroxyethyl acrylate phosphate, the ammonium or alkali metal salt of the acid groups of the above monomer units, and any combination of the above monomers with each other or with other monomers. In addition, monomers which can be polymerized alone or in combination with the above monomers, and upon further treatment of the polymer such as hydrolysis with aqueous sodium hydroxide yield polymers containing the above monomer unit can also be used. Examples of such monomers are acrylonitrile, methacrylonitrile, methyl methacrylate, methyl acrylate, ethyl acrylate, ethyl methacrylate, and the like.

The graft co-polymer may contain from about 15% to 100% or more by weight of the groups attached to the back-bone of the cellulose. Although either natural cellulose, such as cotton linters, or purified wood pulp may be used to form the graft co-polymer, it is preferred to use a regenerated cellulose such as rayon. The graft co-polymer may contain both hydrophilic and hydrophobic groups but it is preferred that at least about 50% by weight of the groups grafted to the cellulose backbone be hydrophilic groups. In general, the greater the number of hydrophilic groups introduced into the structure, the greater the drying problems.

The foregoing objects and others are accomplished in accordance with this invention, generally speaking, by providing a method for removing water from the above-mentioned absorbent cellulosic and starch materials, referred to collectively herein for simplicity as modified polymers, whether in fibrous, granular, or powder form while retaining the absorbency characteristics of the material and its open structure without producing a stiff brittle material wherein a water-miscible, amphiphilic, non-volatile compound is added to the modified polymer while it is still swollen with water and removing the water by evaporation at a temperature where the amphiphilic non-volatile compound is retained in the polymer structure to a significant extent after the water is removed. It has been found that the water-wet modified polymers described herein, and the like, can be dried by evaporation of the water with heat without the disadvantages inherent in the prior art heat drying processes and that a product which is soft and has high watr absorbency and retention characteristics can be produced provided that a water-miscible, amphiphilic, non-volatile material is absorbed into the open polymer structure of the fibrous material before it is oven dried. In addition to being substantially non-volatile and non-reactive with the modified polymers, the amphiphilic material used to displace the water in the modified polymer fiber must contain sufficient hydrophilic groups so that it will not interfere with the entrance of fluid when it is used in a pad for absorbing body fluids and sufficient lipophilic groups to prevent extensive, irreversible hydrogen bonding with the hydrophilic groups of the modified cellulosic or starch materials which will cause collapse of the structure resulting in an undesirable, stiff, brittle material. An amphiphilic material is hereby defined as a compound which contains both hydrophilic and lipophilic groups. Compounds of this type usually belong to the class of surfactants. As in the case of surface activity, the compounds used in this invention require a balance of hydrophilic and lipophilic groups.

This balance of hydrophilic and lipophilic groups is accomplished by varying two parameters—the ratio of one type of group to the other, and the exact chemical structure of each type of group. This combination of variables gives the possibility of hundreds of thousands of amphiphilic compounds, both in regard to surfactant technology, and in regard to practicing this invention. Therefore, in surfactant technology where many diverse property requirements and functions exist, a particular surfactant may or may not be suitable for a specific application. This analogy also applies in regard to this invention i.e., the exact structure of the particular non-volatile amphiphilic compound to be used will depend to some extent on the chemical nature of the modified cellulosic or starch compound, the degree of modification, and the physical nature of the material.

Moreover, since a mixture of two or more surfactants often works better than a single compound, some mixtures of amphiphilic compounds might achieve better results in this invention. Finally, in regard to the exact structure of the amphiphilic materials commercially available, the statement on page 509 in the article on Surfactants (Kirk Othmer, Vol. 19, Chapin E. Stevens) is quite applicable: "Practical surfactant technology deals with mixtures of precisely specified properties, but incompletely defined compositions. Many surfactant products are 'polydisperse'," meaning a preparation containing molecules which are all the same type, but vary only in chain length or in some other structural detail. (R. A. Gibbons, *Nature* 200, Nov. 1963 pp. 665-666).

In regard to practicing the invention, it has been found that amphiphilic compounds having diverse structures of hydrophilic and lipophilic groups act within the general mechanism of preventing collapse of the structure. Furthermore, one type of structure may work well for one type of modified cellulosic or starch compound, but not in another. However, it has been found that the principle of HLB (hydrophilic-lipophilic balance) system, borrowed from surfactant technology, can be a useful tool for selecting a specific amphiphilic compound once the general structure has been chosen. Although the exact HLB number will depend on the general structure of the amphiphilic compound, the chemical nature and amount of the modifying hydrophilic group, the chemical and physical nature of the modifying backbone and the substrate and the form of the modified material, it appears to be generally true that the HLB of compounds useful in practicing the invention lies in the hydrophilic range, which is generally between 11 and 20. In addition, it has been found that three general classes of amphilic compounds offer general performance above that offered by other types of compounds and with different types of hydrophilic modified cellulose or starch materials. The HLB range of these three classes of compounds is also somewhat broader, extending into intermediate range between hydrophilic and lipophilic, which is generally in the numerical range of 9 to 11.

The structures of these three classes of compounds are given below, with a reminder that the generalizations given above in regard to general surfactant technology can apply in these cases also.

1. Carboxylic acid amides having the following general formula:

$$R_1-\underset{\underset{O}{\|}}{C}-N\begin{matrix}R_2\\R_3\end{matrix}$$

where
$R_1 = C_7-C_{17}$ saturated or unsaturated, branched or normal alkyl, pure or mixed.

$$R_2 = (CH_2\overset{R_5}{\underset{|}{C}}HO)_nH \text{ or}$$

$$R_4-\underset{\underset{O}{\|}}{C}-O^- M^+$$

where
n = 1-50

$R_4 = C_1-C_{10}$ alkyl, pure or mixed
$R_5 = H$ or $CH_3$
M = hydrogen, ammonium, or alkali metal
$R_3 = H$ or $R_2$ or $C_1-C_{10}$ saturated or unsaturated, branched or normal alkyl, pure or mixed 2. Dialkylsulfosuccinates having the following general structural formula:

$$R-O-\underset{\underset{O}{\|}}{C}-CH-\underset{\underset{O}{\underset{\|}{}}}{\overset{\overset{O}{\|}}{S}}-O^- M^+$$
$$\underset{RO-\underset{\underset{O}{\|}}{C}-CH_2}{|}$$

wherein
$R = C_6$ to $C_{12}$ saturated, branched or normal alkyl, pure or mixed
M = H, $NH_4$ or alkali metal 3. Ethoxylated alkyl phenols having the following general structural formula:

$$(R)_m-\text{\textlangle phenyl\textrangle}-O(C_2H_4O)_nH$$

wherein
$R = C_8$ to $C_{12}$ tertiary alkyl, pure or mixed.
m = 1 to 2
n = 5 to 20

The above groups may be further illustrated by specific compositions, many available commercially under various trademarks, such as:

1. a. Carboxylic acid amides, e.g., the condensate of lauric acid and diethanolamine plus a minor amount of diethanolamine oleate to help solubilize the amide; (Active No. 2—obtained from Blew Company; now available as Solar Regular from Swift Chemical Company;

b. Ethoxylated fatty amides, e.g., Ethomid HT/60 (mixtures of $C_{15}$, $C_{17}$, and $C_{19}$; 50 moles ethylene oxide (EO) and Ethomid O/15 ($C_{17}H_{33}$; 5 moles EO) both available from Armak Company);

c. The sodium salt of oleoyl sarcoside where $R_1 = C_{17}H_{33}$; $R = CH_2COO^-Na^+$, and $R_2 = CH_3$ (Arkomon A. conc. available from American Hoechst Company); and d. The condensate of hydrogenated cocoanut fatty acid and diethanolamine where R averages $C_{11}H_{23}$ but ranges from $C_7$ to $C_{17}$ and n=1 (Nopcostat 261 from Diamond Shamrock Co.)

2. a. Sodium dioctyl sulfosuccinate (Triton GR-5 available from Rohm & Haas Company, Aerosol OT available from American Cyanamid Co., and Nopcowet 50 available from Diamond Shamrock Co.)

3. Compounds of the class of ethoxylated branched chain alkyl-substituted phenols wherein R may be t-octyl and n is 9 to 10 (Triton X-100 available from Rohm & Haas Co.)

Other specific compounds not in the three classes given above but which have been found to operate within the scope of the invention are described in the Examples.

Thus, in its broadest aspects, the invention contemplates a method for drying cellulosic or starch material modified with an increased number of hydrophilic groups by adding to an aqueous slurry or gel of the modified material, a non-volatile amphiphilic compound which will remain in the modified material when water is removed with heat and thus avoid collapse of the cellulosic or starch structure during the removal of water. If the modified cellulose or starch material is to be put into a definite physical form e.g. by spinning a fiber or filament in a bath of water or coagulant or otherwise adding a gel or suspension of the material to water or a water based solution, the amphiphilic compound may also be incorporated into this solution. The same or different amphiphilic compound may or may not also be added to the gel or suspension of the modified material. For most purposes, any compound of the classes described above having a low vapor pressure at a temperature of 100° C. or higher can be used. The fibers may be dried at any combination of temperature and pressure which will remove the water without complete removal of the hydrophilic compound added thereto, but it will usually be dried at atmospheric pressure at about the boiling point of water.

The product of the invention may be obtained in fibrous or non-fibrous form and can be used to advantage in the manufacture of any article which is required to absorb fluids. Fibers can be used, for example, in pads for absorbing water or body fluids such as surgical sponges, diapers, catamenial tampons and napkins and the like. Unmodified cellulosic or starch materials or even non-hydrophilic materials may be blended with the modified materials in the formation of these articles.

The invention is illustrated by the following examples. All parts are by weight unless otherwise specified.

EXAMPLE I

A sheet of unbeaten, bleached northern softwood kraft pulp is immersed in a solution containing about 30 parts water, about 47 parts urea and about 23 parts orthophosphoric acid. After the sheet has absorbed the solution, it is pressed to reduce the liquid content to about 2 parts per part fiber. The moist sheet is heated in an oven for about 45 minutes at 170° C. The sheet is then dispersed in water and the resulting slurry is filtered and the fibrous mass on the filter is washed free from urea and phosphoric acid. The filter cake thus obtained is dispersed in a 3.7% solution of hydrochloric acid and maintained in the dispersion at from about 60° C. to 70° C. for about ½ hour. The resulting fiber is separated from the aqueous phase and washed free of acid with water. It is then slurried in a 5% aqueous solution of sodium carbonate, filtered and washed to remove excess sodium carbonate. It is then refined in a standardized Valley beater or other type of conventional refiner at 10% consistency for about 30 minutes.

The pH of the refined pulp suspension is then adjusted to about 7.4 with HCl. This suspension is centrifuged to form a gel-like suspension of swollen modified cellulosic fibers at a concentration of about 7.5% by weight in water. One hundred gram portions of the gel are weighed into a cup and 50 grams of water containing 0.75 grams of an amphiphilic compound are added. The mixture is then thoroughly mixed so that the concentration of sodium cellulose phosphate is about 5%. This diluted gel, containing 10% of the amphiphilic compound based on the weight of the modified cellulose, is cast into a cover of a Petri dish and dried in an oven at 75° C. for about 2 hours to form a cake of modified material. A control sample is also prepared in which there is no amphiphilic compound in the added water.

The absorbency and swelling characteristics of the fiber are determined by suspending one portion of the dried fiber in an excess of water and a second portion in a 1% aqueous sodium chloride solution. The Water Retention Value (WRV) and Saline Retention Value (SRV) are determined by separating most of the water and sodium chloride solution, respectively, from the fiber by centrifuging it at 1000 gravities and measuring the amount in grams of liquid per gram of modified pulp retained in the fiber.

TABLE I

| Example No. | Amphi- Philic Compound | WRV g/g | SRV g/g | Structure Class |
|---|---|---|---|---|
| A | None | 3.09 | 1.81 | |
| B | Active No. 2 | 4.17 | 2.15 | (1) |
| C | Triton GR5 | 4.07 | 2.14 | (2) |
| D | Triton X-100 | 3.75 | 2.00 | (3) |

It is apparent from the results reported in Table I that the water absorbency (WRV) and 1% aqueous sodium chloride (SRV) absorbency of the fibers dried in accordance with this invention is greater than it is when the fibers are dried in an oven at the same temperature without the addition of the hydrophilic compound as provided by this invention. In addition, the fibers are not hard and horny, but are soft and fibrous. Hence, the invention provides fibers having optimum absorbency characteristics without the use of a solvent displacement process for drying the fibers.

EXAMPLE II

The procedure of Example I is repeated except that instead of forming a cake of the modified fibers, the gel is then spun into a random pattern web through a IIIA Zenith pump and plastic nozzle with approximately a 0.0031 inch orifice in a similar manner to the procedure described in Example 2 of U.S. Pat. No. 3,997,647. The concentration of the amphiphilic compound is still 10 percent based on the weight of modified cellulosic material. The webs are dried in a forced air oven at 80° C. for 15-20 minutes, cooled, and placed into a plastic bag before testing. A control is made with dilution water only and no amphiphilic compound. In addition, a solvent-dried control made by immersing the web from the "no additive" control into an acetone solvent exchange bath and dried by evaporating off the remaining acetone, again as in Example 2 of U.S. Pat. No. 3,997,647. The absorbency of these webs were determined by the Demand Wettability method (Lichstein, Bernard, International Nonwovens and Disposables Association, 2nd Annual Symposium on Non-Woven Product Development, Mar. 5-6, 1974, Washington, D.C.), where the 4-inch square portions of the webs were placed over an opening in a platform at zero hydrostatic pressure with the stopcock of a modified buret filled with distilled water. The amount of water demanded for an average of 4 determinations is shown in Table II.

TABLE II

| Example No. | Amphiphilic Compound | Structure Class | Demand Wettability ml. Water Per Gram Of Material |
|---|---|---|---|
| A | None | | 15.6 |
| B | None - | | 22.3 |

TABLE II-continued

| Example No. | Amphiphilic Compound | Structure Class | Demand Wettability ml. Water Per Gram Of Material |
|---|---|---|---|
| C | Acetone Exchanged Active No. 2 | (1) | 27.0 |
| D | Triton GR-5 | (2) | 28.6 |
| E | Triton X-100 | (3) | 21.2 |
| F | Nopcowet 50 | (2) | 22.1 |
| G | Nopcostat 261 | (1) | 18.4 |

EXAMPLE III

Webs are spun from a gel in a similar manner as described in Example II except that the webs are spun into aqueous baths containing amphiphilic compounds as described below, and dried at 140° C. The gels may or may not contain an amphiphilic compound, as described below.

BATH PREPARATION

The appropriate amphiphilic compound is dissolved in water. The weight ratio of bath to gel is about 1.5 or higher.

GEL PREPARATION

The gels used contain approximately 6.85% of the modified cellulosic material. Sufficient distilled water containing the amphiphilic compound is added so that the gel was diluted to 6.5% solids. The WRV and SRV values are determined as in Example I and reported in Table III.

In the following table, gel amounts are based on weight of modified cellulosic material, and spinning bath additive amounts are based on weight of bath.

TABLE III

| Sample No. | Amphiphilic Compound Added to Gel | Spinning Bath Composition | Structure Class | SRV g/g |
|---|---|---|---|---|
| A | None | Air | | 1.58 |
| B | None | 65% Dioctyl-sulfosuccinate (Triton GR-5) | (2) | 1.98 |
| C | None | 30% Dioctyl-sulfosuccinate (Triton GR-5) | (2) | 3.74 |
| D | 10% Dioctyl-sulfosuccinate (Triton GR-5) | Air | (2) | 1.72 |
| E | 10% Dioctyl-sulfosuccinate (Triton GR-5) | 65% Dioctyl-sulfosuccinate (Triton GR-5) | (2) (2) | 3.09 |
| F | 10% Dioctyl-sulfosuccinate (Triton GR-5) | 30% Dioctyl-sulfosuccinate (Triton GR-5) | (2) (2) | 4.57 |
| G | None | 50% Ethoxylated (9-10 moles EO) t-octyl phenol (Triton X-100) | (3) | 2.08 |

EXAMPLE IV

A 908-g. sample of cellulose fiber grafted with acrylic acid by the general procedure described in Brickman, supra, is soaked for 5 minutes in 14 l. of 2.0% NaOH solution (ratio of solution to fiber is 20/1 by weight) with agitation by hand. The excess solution is squeezed from the sample between rollers. The above is then repeated twice using soft water in place of NaOH. After the final wash and squeezing, the sample is placed in 0.175% HCL and 1% NaCl solution for 5 minutes with agitation by hand and the excess squeezed out. The sample is pressed between the rollers and 60 g. is placed in the various finish baths listed below in Table IV at a ratio of 25/1 (liquid/fiber) for 5-10 minutes at the noted concentrations. They are then removed, squeezed to remove excess solution, and then placed in an oven at 110° C. Softness of the fiber, indicating the degree of hydrogen bonding and structure collapse is shown in Table IV.

TABLE IV

| Surfactant | Concentration (%) | Structure Class | Softness |
|---|---|---|---|
| A None (control) | | | Hard, matted |
| B Active No. 2 | 0.6 | (1) | Soft, easily separates, better than acetone exchange |
| C Arkomon conc. | 0.6 | (1) | Equal to acetone exchange |
| D Ethomid HT/60 | 0.6 | (1) | Some harsher than C, but separates easier |
| E Triton X-100 | 0.6 | (4) | Better than C |
| F Triton GR-5 | 0.9 | (3) | Like C |
| G Nopcostat 261 | 0.6 | (1) | Generally soft with hard spots and stringy. |

EXAMPLE V

This example illustrates the class of amphiphilic compound derived from oligomeric amphiphilic compounds derived from functional, unsaturated monomers and a hydrocarbon mercaptan. These materials follow the general formula of:

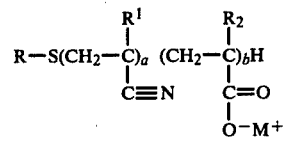

where
R = $C_6$ to $C_{12}$ alkyl
$R_1$ = H or $CH_3$
$R_2$ = H, $CH_3$ or $CH_2COO^-M^+$
a+b = 4 to 50
a/(a+b) = 0 to 0.6 and
M = H, $NH_4$ or alkali metal The procedure of Example II was followed exactly except that the amphiphilic materials used were Polywet KX-1 and Polywet KX-3, both available from Uniroyal and both in the potassium salt form. The differences between these two products due in part to the ratio and amount of the parameters a and b and possibly the R group in the above formula changed the HLB value from 10 for KX-1 to 16 for KX-3. This difference in HLB resulted in a demand wettability value of 13.5 for KX-1, which is even below the value for the heat dried control, and a value of 23.4 for KX-3, which is even better than the acetone exchanged control.

EXAMPLE VI

This example demonstrates the results of varying both the hydrophilic and the lipophilic group within a particular structural group of amphiphilic compounds as well as smaller variations in type of and method of processing a modified cellulosic material. All of the amphiphilic compounds in this example are similar in structure to the Class 3 compounds, and do improve performance under some conditions and in one or more aspects of this invention. For example, Triton X-155 and X-405 show a significant improvement, as measured by secondary swelling, (WRV and SRV), but do not substantially increase the demand wettability over the controls. As seen in Table V there are differences in performance between some compounds of apparently similar chemical structures but from a different commercial source. These differences between the Triton materials from Rohm and Hass and the Igepal series from GAF Corp. can be understood from the article on "Surfactants" by Chapin E. Stevens in Kirk-Othmer Encyclopedia of Chemical Technology, Vol. 19, p. 533. This article emphasizes the mixture of various structures which are necessarily obtained in a given process of manufacture of the alkylphenols. Furthermore, the differences between branched-chain alkylphenols from different sources is pointed out to be as great as or greater than the differences between branched-chain and linear substituted alkylphenols from the same source. As can be seen from Table V and a comparison of the t-octyl phenol (Triton X-100) results in Tables I, II and IV, the more highly branched alkylphenol, i.e., the tertiary structure in the Triton series show the best overall performance. This phenomenon is not surprising in view of the previously stated method of operation of amphiphilic compounds in this invention. However, it is also clear from Table V that, with a given lipophilic group, optimumization of performance can be achieved by adjusting the HLB value of the amphiphilic compound.

TABLE V

| Example No. | Amphiphilic Compound | Structure From Class III R | n | Calculated HLB | Performance Under Example I Conditions WRV | SRV | Performance Under Example II Conditions Demand Wettability | Performance Under Example IV Conditions |
|---|---|---|---|---|---|---|---|---|
| A | None | | | | — | — | 15.6 | — |
| A | Triton X-15 | octyl | 1 | 3.6 | 2.69 | 1.66 | — | — |
| B | Triton X-363 | * | * | 9.1 | 2.75 | 1.77 | — | — |
| C | Triton X-155 | * | * | 12.5 | 3.55 | 2.03 | 15.4 | Like Triton X-100 |
| D | Triton X-405 | octyl | 40 | 17.9 | 4.00 | 2.14 | 16.8 | Like acetone exchanged |
| E | Triton X-705 | octyl | 70 | 18.7 | 3.88 | 2.01 | — | Slight improvement over heat dried control |
| F | Igepal CA-630 | octyl | 9 | 13.3 | 3.51 | 2.14 | 16.8 | Between acetone dried and heat dried control |
| G | Igepal CO-630 | nonyl | 9 | 13.1 | 3.34 | 1.89 | — | Harsher than acetone dried but separates easier |
| I | Igepal CO-887 (Comparative) | nonyl | 30 | 17.4 | 3.02 | 1.87 | — | Only slight improvement over control |
| J | Igepal CA-897 (Comparative) | octyl | 40 | 17.9 | 3.09 | 1.82 | — | — |
| K | Igepal CO-997 (Comparative) | nonyl | 50 | 18.1 | — | — | — | Same as control |
| L | Igepal RC-520 | dodecyl | 8–9 | 12.6 | 2.90 | 1.90 | — | Harsher than acetone but separates easier |

* Not known with certainty.

EXAMPLE VII

This example demonstrates the utility of a variety of amphiphilic compounds which do not fall into the three structural classes described above. The results of these compounds utilized by the methods described in Examples I, II, III, or IV are given in Table VI. The selectivity of the amphiphilic compounds useful in the process is further shown by comparative example F.

TABLE VI

| Example No. | Amphiphilic Compound | Nomenclature or Structure | Example I WRV | SRV | Example III Gel Additive | Spinning Bath Composition | SRV | Example IV |
|---|---|---|---|---|---|---|---|---|
| A | None | | 3.09 | 1.81 | None | Air | 1.58 | Hard, matted |
| | | | | | None | Water | 1.23 | |
| B | Triton W-30 Conc. (Rohm & Haas Co.) | Sodium alkylaryl ether sulfate (27% active solution) | — | — | None | Triton W-30 Conc. | 2.84 | Harsher than acetone dried but separates easier. |
| | | | — | — | 10% Triton W-30 Conc. (active basis) | Air | 1.56 | — |
| | | | — | — | 10% Triton W-30 Conc. (active basis) | Triton W-30 Conc. | 3.88 | — |
| | | | — | — | 10% Triton W-30 Conc. (active | 30% Dioctyl-sulfosuccinate | 3.51 | — |

TABLE VI-continued

| | | | | | Example III | | | |
|---|---|---|---|---|---|---|---|---|
| | | | \multicolumn{2}{c}{Example I} | Gel | Spinning Bath | | |
| Example No. | Amphiphilic Compound | Nomenclature or Structure | WRV | SRV | Additive | Composition | SRV | Example IV |
| | | | | | basis) | (DOSS) (Triton GR-5) | | |
| | | | — | — | 10% DOSS (active basis) | Triton W-30 Conc. | 2.96 | — |
| C | Triton 770 Conc. (Rohm & Haas Co.) | Sodium Alkylaryl polyether sulfate (30% active solution) | — | — | — | — | — | Harsher than acetone dried but separates easier. |
| D | Triton X-200 (Rohm & Haas Co.) | Sodium Alkylaryl polyether sulfate (28% active solution) | — | — | — | — | — | Like acetone dried |
| E | Triton QS-9, sodium salt (Rohm & Haas Co.) | Phosphate ester, sodium salt | — | — | None | 50% Triton QS-9 sodium salt based on active ingredient | 6.26 | — |
| F | Triton QS-9 (Rohm & Haas Co.) (Comparative) | Phosphate ester, acid form (70% active solution) | — | — | None | 50% Triton QS-9 based on active ingredient | 0.46 sticks to screen | — |
| G | Triton DF-20, sodium salt (Rohm & Haas Co.) | Modified ethoxylate, sodium salt form | — | — | None | 50% Triton DF-20 sodium salt based on active ingredient | 2.80 | — |
| H | Triton X-67 (Rohm & Haas Co.) | Alkylpolyether alcohol (100% active) | 4.12 | 2.03 | None | Triton X-67 | 2.41 | Like acetone dried |
| I | Alipal CO-436 (GAF Corp.) | Ammonium salts of sulfated nonylphenoxy-poly(ethyleneoxy) ethanol | — | — | None | 50% Alipal CO-436 | 2.42 | Half between acetone dried and heat dried control |
| J | PEG 300 Mono-palmitate (Armak Co.) | $C_{15}H_{31}\overset{O}{\overset{\|}{C}}O(C_2H_4O)_{6.8}H$ | — | — | — | — | — | Harsher than acetone but separates easier |
| K | PEG 400 Mono-laurate (Armak Co.) | $C_{11}H_{23}\overset{O}{\overset{\|}{C}}O(CHO)_{9.1}H$ | | | 10% PEG Mono-laurate | Air | 2.39 | |
| | | | | | 10% PEG Mono-laurate | 65% Dioctyl-sulfa succinate (Triton GR-5) | 3.11 | — |
| | | | | | 10% PEG Mono-laurate | 30% Dioctyl-sulfa succinate (Triton GR-5) | 3.31 | — |
| | | | | | 10% PEG Mono-laurate | Triton W-30 Conc. | 3.56 | — |
| L | Aerosol A-102 (50% active (American Cyanamide Co.) | Disodium ethoxylated alcohol half ester of sulfosuccinic acid (31% active) | — | — | None | 10% Active aerosol A-102 | Dispersed in spin bath | — |
| | | | | | None | %0% Active Aerosol A-102 | 4.60 | — |
| M | Nopco 2152-P (Diamond Shamrock Co.) | Polyethyeneglycol ester of cocoanut fatty acid plus minor amount of antistatic agent | — | — | — | — | — | Better than acetone drying |
| N | Brij 98 | Polyoxyoxyethylene (20) oleyl ether | Superior to control Example II Demand Wettability | | — | — | — | — |
| O | Ethox CO-25 | ethoxylated (25 Moles EO) castor oil | 17.8 | | — | — | — | Harsher than acetone; separates easier |

Although the invention has been described in detail for the purpose of illustration, it is to be understood that such detail is solely for that purpose and that variations can be made therein by those skilled in the art without departing from the spirit and scope of the invention except as it may be limited by the claims.

I claim:

1. A method for drying chemically modified cellulose or starch materials which comprises mixing the materials with an aqueous solution of at least one amphiphilic compound, which is miscible with water nonvolatile and substantially non-reactive with said modified cellulose and thereafter evaporating the water from the materials at an elevated temperature whereby said amphiphilic compound is retained by said materials and prevents the substantial collapse of the cellulosic structure, thereby avoiding significant reduction in water absorbency or loss of aesthetics of the material.

2. The method of claim 1 wherein the said amphiphilic compound is a surfactant selected from the group consisting of
   a. Carboxylic acid amides having the following general formula:

$$R_1-\overset{\overset{O}{\|}}{C}-N\overset{R_2}{\underset{R_3}{\diagdown}}$$

where
$R_1 = C_7$–$C_{17}$ saturated or unsaturated, branched or normal alkyl, pure or mixed.

$$R_2 = (CH_2\overset{\overset{R_5}{|}}{C}HO)_nH \text{ or}$$
$$R_4-\overset{\overset{O}{\|}}{C}-O^- M^+$$

where
$n = 1$–50
$R_4 = C_1$–$C_{10}$ alkyl, pure or mixed
$R_5 = H$ or $CH_3$
$M =$ hydrogen, ammonium, or alkali metal
$R_3 = H$ or $R_2$ or $C_1$–$C_{10}$ saturated or unsaturated, branched or normal alkyl, pure or mixed
   b. Dialkylsulfosuccinates having the following general structural formula:

$$R-O-\overset{\overset{O}{\|}}{C}-CH-\overset{\overset{O}{\|}}{\underset{\underset{O}{\|}}{S}}-O^- M^+$$
$$R\ O-\overset{\overset{O}{\|}}{C}-CH_2$$

wherein
$R = C_6$ to $C_{12}$ saturated, branched or normal alkyl, pure or mixed
$M = H$, $NH_4$ or alkali metal and
   c. Ethoxylated alkyl phenols having the following general structural formula:

$$(R)_m-\phenyl-O(C_2H_4O)_nH$$

wherein
$R = C_8$ to $C_{12}$ tertiary alkyl, pure or mixed.
$m = 1$ to 2
$n = 5$ to 20

3. The method of claim 2 wherein said elevated temperature is from 60° to 100° C.

4. The method of claim 1 wherein said modified material is a fiber comprising a cellulose graft co-polymer having side chains grafted thereto and containing acrylic acid or methacrylic acid units or salts thereof.

5. The method of claim 1 wherein said modified material has at least one hydrophilic monomer or monomers polymerized therein.

6. The method of claim 1 wherein said modified material is a water wet polymer having an open structure and hydroxyl groups substituted by hydrophilic groups.

7. The method of claim 1 wherein said modified material is a phosphorylated cellulose.

8. The product of the process of claim 1, wherein said modified material is carboxymethylcellulose.

9. A process for drying by evaporation a highly water absorbent chemically modified cellulosic polymer which comprises incorporating in the open polymer structure a water-miscible, amphiphilic, non-volatile compound which is non-reactive with the polymer and evaporating the water from the polymer by thermal means at elevated temperatures whereby said water is removed without collapsing said open structure while retaining the water-miscible, amphiphilic, non-volatile compound in the polymer structure.

10. The process of claim 9 wherein said polymer is a water wet polymer having hydroxyl groups substituted by hydrophilic groups and an open structure which discourages hydrogen bonding.

11. The process of claim 10 wherein the hydrophilic groups are carboxylic acid, phosphoric acid, sulfuric acid, or carboxyl amide groups.

12. The process of claim 10 wherein the polymer is carboxymethylcellulose.

13. The process of claim 9 wherein the polymer is phosphorylated cellulose.

14. The product of the process of claim 10 wherein about 5–20% by weight of said amphiphilic compound is added to said polymer.

15. The process of claim 4 wherein about 0.2–1.0% by weight of said amphiphilic compound is added to said graft copolymer.

16. The process of claim 9 wherein said polymer is spun into an aqueous bath containing about 20–75% by weight of said amphiphilic compound.

17. The process of claim 4 wherein said side chains are acrylic acid or methacrylic acid units or salts thereof.

18. The product of the process of claim 9.

* * * * *